United States Patent [19]

Baron et al.

[11] Patent Number: 4,595,588

[45] Date of Patent: Jun. 17, 1986

[54] NATURAL INHIBITOR THAT PROTECTS AGAINST VIRAL INFECTIONS

[75] Inventors: Samuel Baron, Dickinson; M. Louese McKerlie, Galveston, both of Tex.

[73] Assignee: Board of Regents, The University of Texas System, Austin, Tex.

[21] Appl. No.: 613,640

[22] Filed: May 24, 1984

[51] Int. Cl.[4] .................... A61K 39/00; A61K 35/12; A61K 49/00

[52] U.S. Cl. ........................................ 424/89; 424/88; 424/93; 514/21; 435/948; 435/240; 435/235

[58] Field of Search ................. 424/88, 89, 93; 514/2, 514/21; 435/948, 240, 235

[56] References Cited

U.S. PATENT DOCUMENTS

| | | | |
|---|---|---|---|
| 4,278,662 | 7/1981 | Lohmann et al. | 424/89 |
| 4,315,914 | 2/1982 | Arakawa et al. | 424/89 |
| 4,341,763 | 7/1982 | Zygraich | 424/89 |
| 4,452,734 | 6/1984 | Larson et al. | 424/89 |
| 4,508,708 | 4/1985 | Wezel | 424/89 |

OTHER PUBLICATIONS

Broadly Active Inhibitor of Viruses Spontaneously Produced by Many Cell Types in Culture, Infection and Immunity, May, 1981, pp. 449–453.
Cell-Produced Viral Inhibitor: Possible Mechanism of Action and Chemical Composition, Infection and Immunity, May 1981, pp. 454–457.
The Third Annual International Congress for Interferon Research, Abstracts, Nov. 1–3, 1982.
Abstracts of the 1982 ICAAC, p. 142.

*Primary Examiner*—Thomas G. Wiseman
*Assistant Examiner*—Garnette D. Draper
*Attorney, Agent, or Firm*—Arnold, White & Durkee

[57] ABSTRACT

A treatment and prophylaxis of viral infections in mammals is provided. The method involves administering an amount of a contact-blocking viral inhibitor (CVI) sufficient to elevate the concentration of the viral inhibitor in the mammal's tissue above the naturally occurring concentration in that same tissue. Methods for purifying and concentrating CVI are presented. The cellular viral inhibitor is characterized by broad antiviral activity, potency, reversible inhibition of viral attachment, cross species activity and molecular size. Natural levels of CVI range from 6 U/0.1 ml in tears to 400 U/0.1 ml in gastric secretions, with titers between these ranges found in colostrum, milk, plasma, saliva and urine. Biochemical characterization of the CVI indicates that it resists denaturation by heat, acid and alkali, and it exhibits a molecular size on the order of 2500 daltons.

8 Claims, No Drawings

NATURAL INHIBITOR THAT PROTECTS AGAINST VIRAL INFECTIONS

BACKGROUND OF THE INVENTION

The present invention details an antiviral regimen as an approach to the prophylaxis against or treatment of a number of viral infections in mammals using a partially purified viral inhibitor, CVI.

Advances in the pharmacologic treatment of viral infections have been slow in coming and indeed very few efficacious antiviral agents presently exist. Amantadine is showing some success but its activity appears to be limited to the influenza $A_2$ strains. The antimetabolite antiviral agents, such as Idoxuridine and Cytarabine, are hampered by narrow spectrum of activity and potentially severe side effects. Methisazone is receiving some support for its use against some pox and vaccinia strains, but its use in pox infections is limited to prophylaxis. In general, none of these antiviral agents show any broad spectrum use and are therefore indicated in only a very few cases.

Interferon and interferon inducers represent a new approach to the treatment of viral infections. These agents have led the way into broad spectrum antiviral therapy. Interferon induction, usually mediated by a polyanionic pyran copolymer or double-stranded RNA from a synthetic source, has been shown to promote cellular resistance to a number of viral infections. The use of interferon directly in human beings has shown some promise as well in early clinical trials. Yet, it should be noted that interferon research is still in its infancy and early claims may be shown to have been overly optimistic.

The present invention proposes a new approach to antiviral therapy using a broad spectrum viral inhibitor, designated CVI (contact-blocking viral inhibitor), found in a number of cell types and sources and readily distinguishable from interferon. CVI has been found to be present in the cell culture media of a number of cell and tissue types, including primary and secondary mouse embryo cells, continuous human HeP-2 cells, secondary human lung, and human thyroid cells, (1981, Infect. Immun. 32:449-453; 1981, Infect. Immun. 32:454-457). In the prior publications it has been demonstrated that an antiviral activity was repeatedly present in the culture media (Hanks minimal essential medium supplemented with 10% fetal bovine serum, penicillin-streptomycin, and 0.075% bicarbonate) removed from the various cell lines after a 24 hour incubation period; the antiviral activity was not detectable in culture medium which had not been exposed to cells. This suggests that the antiviral activity is likely produced by the various cells and secreted into the surrounding media.

Quantification and spectrum of the antiviral activity is determined using a microtiter plaque reduction assay (Table 1, footnote b of 32 Infect. Immun. page 450 (1981)). Mouse embryo cultures generally produced the highest levels of inhibitory activity, human lung produced the next highest levels, and human HeP-2, skin-muscle, and thyroid cells produced less activity. Little or no activity was detected in human U amnion and hamster BHK-21 cells.

Broad antiviral activity was demonstrated in vitro against a number of different viruses: vaccinia virus, polio virus type I, herpes simplex virus, sindbis virus, mengo virus, influenza virus and vesicular stomatitis virus. Inhibitory titers of each CVI preparation was dependent on the particular virus that was challenged. CVI isolated from mouse embryo cells shows the highest inhibitory activity against vaccinia virus followed by vesicular stomatitis and polio I viruses whereas antiviral isolates from Human HeP-2 demonstrated a higher activity against polio I virus. Of course, most antiviral substances, as demonstrated in vitro do not correlate with in vivo activity and clinical efficacy.

CVI preparations are also shown to lack cell species specificity of inhibitor action. Inhibitor produced and titered in mouse embryo or human HeP-2 cells are capable of inhibiting vaccinia virus replication in the heterologous species, indicating the absence of a species barrier. Thus, it is not necessary, in contrast to interferon, to produce the inhibitor from cells that are of the homologous species as the one to be treated. The practical implications being that human tissues or human cells in culture will not be necessary for the isolation of a CVI preparation that is active in man.

The problem addressed by the present invention is how this in vitro activity may best be translated into in vivo activity. Thus the present invention provides an effective therapeutic approach to the treatment of viral infections.

SUMMARY OF THE INVENTION

A method for the prophylaxis and treatment of viral disease in mammals is provided. The method involves administering an amount of contact-blocking viral inhibitor sufficient to elevate the concentration of the viral inhibitor in the mammal's tissue above the naturally occurring concentration in that same tissue.

DETAILED DESCRIPTION OF THE INVENTION

In accordance with the invention, the applicant herein details the preferred steps necessary for the isolation of the viral inhibitor, CVI, in essentially purified form. Further, the biochemical characterization of the viral inhibitor is provided. These characterizations demonstrate that the present viral inhibitor is distinguishable from other known viral inhibitor substances. Further, in order to demonstrate the usefulness of this invention, the Applicant discloses examples of the invention's practice in vivo.

Antiviral activity was initially found to be present in culture media that had been exposed to various cell culture lines. (1981, Infect. Immum. 32:449-453; 1981, Infect. Immum. 32:454-457). The following viral plaque reduction assay was used to titer the antiviral activity extracted from the various test sources and is further used in the quantification and identification of activity during the isolation process:

Virus. Vaccinia virus strain IHDE propagated in chick embryo cells, poliovirus type I Mahoney strain propagated in VERO cells, and vesicular stomatitis virus (VSV) Indiana strain propagated in chick embryo cells, were used. The stock viruses were frozen in aliquots at $-70°$ C. until used.

Titration of inhibitor samples. The titrations were done using vaccinia, polio or VS viruses. For titration with vaccinia virus, mouse L929 cells were grown to confluency in microtest II plates (Falcon Plastics, Oxnard, Calif., 93030 USA). Serial dilutions of each inhibitor sample were made by mixing 0.1 ml of the sample with 0.1 ml minimum essential medium containing 2% fetal bovine serum in duplicate wells followed by addition of 0.025 ml of vaccinia virus containing 30–50 plaque forming units (pfu). Cultures were incubated overnight at 37° C. in 4% $CO_2$ atmosphere. When plaques were visible microscopically, cells were stained with crystal violet. The inhibitory titer was calculated as the highest dilution of the sample which inhibited 50% of viral plaques in the continuous presence of the inhibitor. Titers are expressed as units/0.1 ml or 0.1 gm of original undiluted samples. Similar titrations were done using polio and VS viruses cultured in HeP-2 and WISH or mouse L cells, respectively. After 1.5 hours adsorption at 37° C., the remaining inhibitor and unadsorbed virus were decanted and the cultures overlayed with methyl cellulose. As with other plaque reduction assays for antibody and interferon, a significant difference in CVI titer in the same test is greater than two fold, and in different tests is greater than four fold.

To determine whether the inhibitor induced a durable antiviral effect in cells, cultures treated with inhibitor overnight were washed three times with nutrient medium before virus challenge.

Table I is exemplary of the level of CVI activity normally detected in the culture medium removed from Mouse embryo and Human HeP-2 cells in culture.

TABLE I

| Cell type used for production of inhibitor | Challenge Virus | Cell type used for assay of inhibitor | Titer of inhibitor (U/0.1 ml) |
| --- | --- | --- | --- |
| Mouse embryo | Vaccinia | Human WISH | 32 |
| | Polio I | Human WISH | 4 |
| | Vesicular stomatitis | Human WISH | 6 |
| Human HeP-2 | Vaccinia | Human HeP-2 | 12 |
| | Polio I | Human HeP-2 | 32 |

Further studies indicated that CVI activity is present in a wide spectrum of tissues and biological fluids and not limited to tissue culture cells per se. Table II is illustrative of this finding.

TABLE II

| Sample | Units/0.1 ml of Inhibitory Activity* |
| --- | --- |
| Human Serum | 128 |
| Human Fetal Liver Extract | 128 |
| Human Fetal Heart Muscle Extract | 64 |
| Human Fetal Spleen Extract | 32 |
| Human Fetal Skeletal Muscle Extract | 8 |
| Human Fetal Pancreas Extract | 8 |
| Human Colostrum | 128 |
| Human Mature Milk | 64 |
| Mouse Liver Extract | 16 |
| Human Fetal Lung Culture Fluid (CVI Control) | 32 |
| Mouse Embryo Culture Fluid (CVI Control) | 32 |

*Inhibitory activity assayed by virus plaque reduction with poliovirus on Hep-2 cells.

Isolation of CVI. The antiviral agent, CVI, can be isolated from any source having demonstrable CVI activity. Preferred sources are those containing higher amounts of activity resulting in more consistently pure CVI. The applicant has determined that a crude porcine gastric extract is a suitable starting point.

The crude gastric preparation containing antiviral activity is dissolved in deionized water to a final concentration of 15 grams percent. The resulting acidic solution (pH 4.3–4.8) is placed in a boiling water bath for 30 minutes to inactivate proteolytic enzymes and other heat-sensitive antiviral substances such as Interferon. The boiled solution is then centrifuged to precipitate denatured material. The supernate is collected and filtered through a 0.45 micron membrane.

The filtered supernate is adjusted to pH 4.0 with glacial acetic acid. Fifteen milliliters of the acidified material containing antiviral activity is then applied to a 2.5×30 cm column of SP-Trisacryl M strong cation exchange resin which has been equilibrated with 10 mM $NaC_2H_3O_2$, pH 4.0. The column is flushed with equilibration buffer followed by development with a linear gradient from 10 nM $NaC_2H_3O_2$, pH 4.0 to 0.5M $NaC_2H_3O_2$, pH 8.0. UV-absorbing peaks with antiviral activity are pooled and lyophilized to remove the volatile buffer salts.

The lyophilized antiviral material is dissolved in 20 mM $NaC_2H_3O_2$, pH 8.5 and applied to a 1.5×20 cm column of DEAE-Sephacel weak anion exhange resin which has been equilibrated in the same buffer. The column is flushed with equilibration buffer prior to development with a linear gradient from 20 mM $NaC_2H_3O_2$, pH 8.5 to 0.5M $NaC_2H_3O_2$, pH 4.0. Peaks containing antiviral activity are pooled and lyophilized.

Lyophilized CVI is dissolved in 0.1% $NH_4HCO_3$ and applied to a 1.0×50 cm column of Bio Gel P-6 size exclusion resin equilibrated with the same buffer. The column is developed with the same buffer; the antiviral activity is located, pooled, and lyophilized. The resulting material is greater than 90% pure when compared to the starting material.

Biochemical and biological characterization of CVI. The antiviral substance exhibits many unique biological and biochemical properties which allow it to be distinguished from other substances exhibiting antiviral activity. Characteristics which serve to distinguish CVI include (a) lack of species specificity, (b) broad antiviral activity, (c) low molecular weight, (d) stable at pH and temperature extremes, (e) lack of induction of stable antiviral activity in cells.

(a) Lack of species specificity: CVI activity obtained from one cell type or tissue source is active in preventing viral infections in heterologous tissue or cell types. For example, CVI activity found in human serum will inhibit viral infections in vitro when tested on either mouse L cells or Human Hep-2 cells. Likewise, CVI isolated from Mouse liver extract will inhibit viral infections in both of these cell types as well.

(b) Broad antiviral activity: CVI activity obtained from a particular cell or tissue type is active against a wide spectrum of viral infections, including vaccinia, vesicular stomatitis (VSV) and poliovirus I. This finding, along with the lack of species specificity discussed in (a) above is demonstrated in Table III.

TABLE III

| | Virus: | Units/0.1 ml of Inhibitory Activity* | | |
| --- | --- | --- | --- | --- |
| Sample | Cells: | Vaccinia Mouse L | VS Mouse | Polio Human Hep-2 |
| Human Serum | | 80 | 160 | 64 |
| Human Fetal Liver Extract | | 128 | 64 | 32 |
| Human Colostrum | | 190 | 200 | 120 |
| Human Mature Milk | | 64 | 64 | 32 |
| Mouse Liver Extract | | 64 | 32 | 16 |
| Human Fetal Lung Culture Fluid (CVI Control) | | 128 | 64 | 128 |
| Mouse Embryo Culture Fluid | | 128 | 64 | 64 |

TABLE III-continued

| | | Units/0.1 ml of Inhibitory Activity* | | |
|---|---|---|---|---|
| Sample | Virus:<br>Cells: | Vaccinia<br>Mouse L | VS<br>Mouse | Polio<br>Human Hep-2 |
| (CVI Control) | | | | |

*Inhibitory activity assayed by virus plaque reduction with vaccinia virus, vesicular and poliovirus on mouse L, mouse L and human HEP-2 cells, respectively.

(c) Low molecular weight: In attempting to concentrate the antiviral activity found in physiological fluids by dialysis against high molecular weight solids (Aquacide II, Calbiochem), CVI activity is invariably lost, even when retentive (3,500 dalton MW cut off) dialysis membranes are employed. Where CVI preparations are dialyzed against a small volume (500 ml) of distilled water and subsequently lyophilized, antiviral activity is found in the lypholizate, with little or no activity remaining in the retained material. CVI activity is therefore associated with a small molecular weight species. The size by gel filtration chromatography of the inhibitory molecule was compared for mouse embryo tissue culture CVI, human urine CVI and bovine milk CVI preparations. In all cases the major peak of inhibitory activity corresponded to an apparent molecular mass of 2,500–3000 daltons. When CVI activity against more than one virus (vaccinia virus, herpes simplex type 1 virus) was determined for the same column fractions, inhibitory activity was found in the same fraction. The antiviral activity was attributed to CVI in each case by characterizing the peaks with respect to the defining properties of CVI: prevention of viral attachment, lack of animal cell species specificity, reversible inhibitory activity, failure to act through cell activation, and failure to be inactivated by incubation at 100° C. for 30 minutes.

(d) Stable at pH and temperature extremes. Studies conducted by the Applicant have demonstrated that CVI is highly resistant to pH and temperature extremes. Stability to high temperature is shown by the absence of any significant, systematic loss of activity after incubation of CVI samples at 100° C. for 0.5 hours when compared to samples incubated at 4° for a corresponding length of time as noted in Table IV.

TABLE IV

| CVI containing | Virus | | | | | |
|---|---|---|---|---|---|---|
| | Vaccinia[b] | | Herpes[c] | | Polio[d] | |
| Specimen[a] | 4° | 100° | 4° | 100° | 4° | 100° |
| Milk, Bovine | 27 | 45 | 32 | 81 | 50 | 50 |
| Plasma, Human | 150 | 138 | ND | ND | 100 | 27 |
| Urine, Human | 32 | 64 | 36 | 66 | 25 | 25 |
| Mouse Embryo Tissue Culture Fluid | 128 | 128 | ND | ND[e] | 172 | 217 |

[a]Titer in units/0.1 ml.
[b]Assayed on mouse L-929 cells
[c]Assayed on rabbit skin cells
[d]Assayed on Human Hep-2 cells
[e]ND = not determined Resistance to acid and alkaline denaturation was determined by adjusting the pH of duplicate aliquots of CVI containing material with 6N NaOH or 6N HCl followed by incubation at the appropriate pH for 2 hr at 37° C. Samples of pH sensitive murine interferon were incubated in parallel as positive controls. After incubation, samples were neutralized and assayed for remaining CVI (or interferon) activity. Table V summarizes the results.

TABLE V

| CVI containing<br>Specimen | Titer (units/0.1 ml) after Treatment for 2 Hours at 37° at pH[a] | | | | | | | | |
|---|---|---|---|---|---|---|---|---|---|
| | 1 | 2 | 3 | 5 | 7 | 9 | 11 | 12 | 13 |
| Bovine Milk | 26 | 38 | 32 | 25 | 29 | 24 | 42 | 36 | 16 |
| Bovine Milk Fraction[b] | ND[c] | 116 | 107 | 96 | 91 | 92 | 92 | 82 | 102 |
| Human Plasma | 39 | 59 | 47 | 95 | 105 | 182 | 169 | 192 | 100 |
| Mouse Embryo Tissue Culture | 32 | 32 | 16 | 32 | 32 | 31 | 12 | 9 | 15 |

[a]Assayed on mouse L cells against vaccinia virus after neutralization to pH 7.
[b]Concentrated high activity fraction from gel filtration chromatography.
[c]ND = not determined (e) Lack of induction of stable antiviral activity. CVI inhibits viral infection in a transient fashion. Consequently, antiviral activity is a function of the CVI molecule's continued presence at the site of infection. In contrast to the action of interferon, when cells treated with CVI are washed, cellular resistance to viral infection ceases:

TABLE VI

| CVI-containing<br>Sample | Units/0.1 ml of<br>Inhibitory Activity* | |
|---|---|---|
| | Unwashed | Washed |
| Human Serum | 80 | <20 |
| Human Fetal Liver Extract | 128 | <10 |
| Human Colostrum | 80 | <10 |
| Human Mature Milk | 160 | <20 |
| Mouse Liver Extract | 64 | <10 |
| Human Fetal Lung Culture Fluid (CVI) | 256 | <10 |
| Mouse Embryo Culture Fluid (CVI) | 256 | <10 |

*Cultures were treated with 128 units/0.1 ml of inhibitor preparations for 1 hours at 37° C., washed 3 times and then infected with vaccinia virus. Inhibitory activity assayed by virus plaque reduction with vaccinia virus on mouse L cells.

The removal of inhibitory activity by washing away CVI occurs with most of the viruses tested. However, when influenza and varicella-zoster viruses were used a residual antiviral activity occurred after washing.

The preceding biochemical and biological observations demonstrate that CVI is distinguishable from other recently described viral inhibitors as summed up in Table VII.

TABLE VII

CHARACTERISTICS THAT DISTINGUISH CVI FROM OTHER VIRAL INHIBITORS

| Property | Inhibitor CVI (12, 14)[a] | Antibody (15) | Interferon (16) | Myxovirus inhibitors (1, 3, 5, 6, 11) | Togavirus inhibitors (3, 5, 7, 11,) | Vaccinia virus inhibitor (3, 5, 11, 17) | Paramyxovirus inhibitor (1, 3, 5, 11) | Inhibitor in milk (8) | Misc. inhibitors (2, 3, 5, 9, 11, 18) |
|---|---|---|---|---|---|---|---|---|---|
| Nonspecific inhibition of viruses | + | 0 | + | 0 | 0 | ? | 0 | + | ? |
| Low molecular weight (2500) | + | 0 | 0 | 0 | 0 | ? | 0 | 0 | 0 or ? |
| Stable at 100° C. | + | 0 | 0 | 0 | 0 | ? | 0 | 0 | 0 or ? |
| Stable in lipid solvents | + | 0 | 0 | + | 0 | ? | 0 | ? | +or 0 |
| Activity in cells of heterologous species | + | + | 0 | + | + | + | + | + | + |
| Induction of stable antiviral activity in cells | 0 | 0 | + | 0 | 0 | ? | 0 | ? | ? |
| Produced spontaneously in absence of infection | + | 0 | 0 | + | + | + | + | + | + |
| Reversible inhibition of viruses | + | 0 | 0 | + | + | ? | ? | ? | ? |

[a]Reference numbers in parentheses refer to references numbered below.
? - insufficient information is available to make this comparison
+ - the compared inhibitor exhibits this property
0 - the compared inhibitor does not exhibit this property 1. Tamm I, Horsfall FL Jr. A mucoprotein derived from human urine which reacts with influenza, mumps and Newcastle disease viruses J Exp Med 95:71–97, 1952.
2. Holland JJ, McLaren LC. The mamalian cellvirus relationship II. Adsorption: reception and eclipse of poliovirus J Exp Med 109:487–504, 1959.
3. Smorodintsev AA. Basic mechanisms of nonspecific resistance to viruses in animals and man. Adv Virus Res 7:327–376, 1960.
5. Wasserman FE. Methods for the study of viral inhibitors Methods Virol 4:53–92, 1968.
6. Krizanova O. Rathova V. Serum inhibitor of myxovirus Curr Topics in Microbiol Immunol 47:125–151, 1969.
7. Falker WA, Diwan AR, Halstead SB. A lipid inhibitor of Dengue virus in human colostrum and milk; with a note on the absence of anti dengue secretory antibody. Arch Virol 47:3–10, 1975.
8. Mathews THJ, Lawrence MK, Nair CDG, Tyrrell DAJ. Antiviral activity in milk of possible clinical importance. Lancet 1:1387–1389, 1976.
9. Welsh JK, Arsenakis M, Coelen RJ, May JT. Effect of antiviral lipids. Heat and freezing on the activity of virsuses in human milk. J Infect Dis 140:322–328, 1979.
11. Kumar S, Baron S. Non-interferon cellular products capable of virus inhibition. Tex Rep Biol Med 41:395–401, 1982.
12. Baron S, McKerlie L. A broadly active inhibitor of viruses spontaneously produced by many cell types in culture. Infect Immun 32:449–453, 1981.
14. Coppenhaver DH, Baron JL, McKerlie ML, Sabados J, Baron S. Size and stability of a naturally occuring virus inhibitor. Antimicrob Agents Chemother 25:646–649.
15. Svehage S-E. Diversity of antibodies formed against viruses. Proceedings of the 2nd meeting of the Federation of European Biochemical Societies, Vienna. In: Anader B, ed. Univ of Toronto, Pergamon, Vol 1:p 301, 1967.
16. Baron S, Dianzani F, Stanton GJ. General considerations of the interferon system. Tex Rep Biol Med 41:1–7, 1982.
17. Buckler CE, Baron S. Antiviral action of mouse interteron in heterologous cells. J Bacteriol 91:231–235, 1966.
18. Fujisaka M, Uchida S, Kohima M, Hotts S, Kuroda H. Antiviral substances extractable from *streptococcus*; its in vitro activities and some biological characteristics Kobe J Med Sci 24:99–114, 1978.

The Applicant has made the observation that CVI is naturally present in a wide range of organisms and further, that it is present throughout the body tissues and fluids of those various organisms. Using the microtiter virus plaque reduction assay, the natural levels of CVI in human tissues ranged from a low of 6 units/0.1 ml in tears to a high of 400 units/0.1 ml in gastric secretions. Titers in colostrum, milk, plasma, saliva, and urine fell between these two extremes. It would normally be expected that antiviral molecules which are continuously present in an uninfected organism, and which are not elicited in response to a specific virus challange, would prove ineffective in the treatment of viral diseases. This is apparently not the case for the antiviral substance CVI.

The present invention pertains to the finding that, by raising the in vivo titer of CVI normally found in an organism to some level above such naturally occurring level, that resistance to or elimation of viral diseases is effected. More specifically, the present invention demonstrates that by administering sufficient CVI to an organism such that the total level of CVI present in that organism or such that the level of CVI in a particular affected area or organelle of that organism is increased to at least 10 fold over that CVI level naturally occurring in that organism or area, significant resistance to viral infection may be achieved.

The following examples are submitted by the Applicant in support of this invention.

EXAMPLE I

When samples of Semliki Forest virus are premixed with CVI, a corresponding increase in the total amount of virus needed to achieve an LD$_{50}$ (dose required for 50% mortality) in newborn Swiss mice is observed.

Thus, as indicated in the following chart, if a Semliki Forest virus dilution of $10^{6.8}$ is required to achieve 50% mortality in 12 days in Swiss mice, a concurrent administration of 182 units CVI/ml inoculum will require the reduced dilution in virus of $10^{6.3}$ (exp. 1) or $10^{5.3}$ (exp. 2) in order to achieve a 50% mortality.

| Exp. | Site of Infection | CVI Units/0.1 ml | LD$_{50}$ Titer | Fold Reduction of Viral Titer |
|---|---|---|---|---|
| 1 | I.P. | 0 | $10^{6.8}$ | — |
|   |      | 182 | $10^{6.3}$ | 3 |
| 2 | I.P. | 0 | $10^{6.7}$ | — |
|   |      | 182 | $10^{5.3}$ | 25 |

*CVI in milk extract or placebo was mixed with each Semliki Forest Virus dilution and inoculated intraperitioneally into weanling Swiss mice. Lethal dose 50% (LD$_{50}$) was calculated.

EXAMPLES II

In this example, the Applicant demonstrates the successful reduction of mortality in Swiss mice that had been inoculated with a constant amount of Influenza virus and increasing levels of CVI. Specifically, the mice were inoculated with 8 times the amount of virus necessary to achieve an LD$_{50}$. Accordingly, it was observed that when no CVI was included in the inoculum that a mortality rate of 100% was observed. Yet, when only 182 units CVI/ml. inoculum was included, the mortality rate was reversed, resulting in a 100% survival rate. The highest level in the following chart, 364 CVI units/ml., represents an amount of CVI somewhat greater than a 10 fold increase in the naturally occurring CVI level found in mice.

| CVI/Units/0.1 ml | % Mortality* |
|---|---|
| 0 | 100 |
| 364 | 0 |
| 182 | 0 |

10 mice per group. CVI in milk extract or placebo was mixed with each influenza A2 virus dilution and inoculated intranasally into weanling Swiss mice.

The foregoing description of the invention has been directed to particular embodiments for purposes of explanation and illustration. It will be apparent, however, to those skilled in the art that many modifications and changes in the processes of preparing and implementing the described embodiments may be made without departing from the essence of the invention as defined by the following claims.

What is claimed is:

1. A method for treating a mammal infected with a virus comprising administering to the mammal an antiviral composition comprising a therapeutically effective amount of cellular viral inhibitor having the characteristics of
   (a) lacking species specificity in that the cellular viral inhibitor obtained from one species cell or tissue source is active in heterologous cells or tissue,
   (b) broad antiviral activity against a number of different viruses including vaccinia virus, polio virus type I, herpes simplex virus, sindbis virus, mengo virus, influenza virus, and vesicular stomatitis virus,
   (c) an apparent molecular mass ranging from about 2500 to 3000 daltons as determined by gel filtration chromatography,
   (d) temperature stability between 100° C. and 4° C.,
   (e) stable between pH 1 and 13 and
   (f) produced spontaneously in tissue absent viral infection;
together with a pharmaceutically diluent, said administered amount of the cellular viral inhibitor sufficient to elevate the concentration of said cellular viral inhibitor in the mammal's virally infected tissue above the naturally occurring concentration therein.

2. A method according to claim 1 wherein the concentration of cellular viral inhibitor in the mammal's tissue is elevated to a concentration that is 5-10 fold higher than that naturally occurring therein.

3. The method according to claim 1 wherein the viral infection is influenza virus (ortho myxoviruses), Semliki Forest virus (togaviruses), vesicular stomatitis virus (rhabdoviruses), polio virus and mengovirus (picornaviruses), vaccinia virus (poxviruses), and herpes simplex virus (herpes viruses).

4. A method of prophylaxis against viral disease in mammals comprising administering to the mammal an antiviral composition comprising a prophylactically effective amount of cellular viral inhibitor having the characteristics of
   (a) lacking species specificity in that the cellular viral inhibitor obtained from one species cell or tissue source is active in heterologous cells or tissue,
   (b) broad antiviral activity against a number of different viruses including vaccinia virus, polio virus type I, herpes simplex virus, sindbis virus, mengo virus, influenza virus, and vesicular stomatitis virus,
   (c) an apparent molecular mass ranging from about 2500 to 3000 daltons as determined by gel filtration chromatography,
   (d) temperature stability between 100° and 4° C.,
   (e) stable between pH 1 and 13 and
   (f) produced spontaneously in tissue absent viral infection;
together with a pharmaceutically acceptable diluent, said administered amount of the cellular viral inhibitor sufficient to elevate the concentration of the cellular viral inhibitor above the naturally occurring concentration thereof in said mammal.

5. A method according to claim 4 wherein the concentration of cellular viral inhibitor in the mammal's tissue is elevated to a concentration that is 5-10 fold higher than that naturally occurring therein.

6. The method according to claim 4 wherein the viral infection is influenza (orthomyxoviruses), Semliki Forest virus (togaviruses), vesicular stomatitis virus (rhabdoviruses), polio virus and mengovirus (picornaviruses), vaccinia virus (poxviruses), and herpes simplex virus (herpes viruses).

7. The method of claim 1 wherein the antiviral composition is administered intraperitoneally or intranasally.

8. The method of claim 4 wherein the antiviral composition is administered intraperitoneally or intranasally.

* * * * *

UNITED STATES PATENT AND TRADEMARK OFFICE
CERTIFICATE OF CORRECTION

PATENT NO. : 4,595,588

DATED : June 17, 1986

INVENTOR(S) : Samuel Baron and M. Louese McKerlie

It is certified that error appears in the above-identified patent and that said Letters Patent is hereby corrected as shown below:

Column 9, line 39, insert --acceptable-- after "pharmaceutically"

Signed and Sealed this

Sixteenth Day of September 1986

[SEAL]

Attest:

DONALD J. QUIGG

Attesting Officer

Commissioner of Patents and Trademarks